United States Patent
Ceccaldi et al.

(10) Patent No.: US 10,997,717 B2
(45) Date of Patent: May 4, 2021

(54) METHOD AND SYSTEM FOR GENERATING A CONFIDENCE SCORE USING DEEP LEARNING MODEL

(71) Applicant: Siemens Healthcare GmbH, Erlangen (DE)

(72) Inventors: Pascal Ceccaldi, Princeton, NJ (US); Peter Mountney, London (GB); Daniel Toth, Twickenham (GB); Serkan Cimen, Stockport (GB)

(73) Assignee: Siemens Healthcare GmbH, Erlangen (DE)

( * ) Notice: Subject to any disclaimer, the term of this patent is extended or adjusted under 35 U.S.C. 154(b) by 191 days.

(21) Appl. No.: 16/263,076

(22) Filed: Jan. 31, 2019

(65) Prior Publication Data
US 2020/0250812 A1    Aug. 6, 2020

(51) Int. Cl.
*G06T 7/00*    (2017.01)
*G06N 3/08*    (2006.01)
*G06T 7/10*    (2017.01)
*G16H 30/40*    (2018.01)
*G06K 9/46*    (2006.01)
*G06T 7/30*    (2017.01)

(52) U.S. Cl.
CPC .............. *G06T 7/0012* (2013.01); *G06N 3/08* (2013.01); *G06T 7/10* (2017.01); *G16H 30/40* (2018.01); *G06K 9/46* (2013.01); *G06T 7/30* (2017.01); *G06T 2207/20081* (2013.01); *G06T 2207/20104* (2013.01)

(58) Field of Classification Search
None
See application file for complete search history.

(56) References Cited

U.S. PATENT DOCUMENTS

| | | | |
|---|---|---|---|
| 10,282,546 B1* | 5/2019 | Parikh | G06N 3/08 |
| 2009/0262996 A1* | 10/2009 | Samsonov | G01R 33/5611 382/130 |
| 2015/0238148 A1* | 8/2015 | Georgescu | G06K 9/4628 600/408 |
| 2016/0174902 A1* | 6/2016 | Georgescu | G06T 7/0012 600/408 |
| 2016/0335478 A1* | 11/2016 | Bredno | A61B 17/3423 |
| 2017/0264902 A1* | 9/2017 | Ye | G06N 3/0454 |
| 2018/0012463 A1* | 1/2018 | Chaudhry | H04N 7/181 |
| 2018/0174042 A1* | 6/2018 | Srinivasa | G06N 3/049 |
| 2018/0232870 A1* | 8/2018 | Jo | G01N 25/72 |
| 2019/0042882 A1* | 2/2019 | Kim | G06N 3/0454 |
| 2019/0130305 A1* | 5/2019 | Sivertson | G06N 5/022 |
| 2019/0164313 A1* | 5/2019 | Ma | G06K 9/6256 |
| 2019/0251713 A1* | 8/2019 | Chen | G06N 3/084 |
| 2019/0258878 A1* | 8/2019 | Koivisto | G05D 1/00 |
| 2019/0340541 A1* | 11/2019 | Watson | G06N 3/084 |
| 2019/0369191 A1* | 12/2019 | Gong | G01R 33/5608 |
| 2020/0005133 A1* | 1/2020 | Zhang | G06N 3/0454 |

(Continued)

*Primary Examiner* — Gandhi Thirugnanam
(74) *Attorney, Agent, or Firm* — Schiff Hardin LLP (57) ABSTRACT

In a system and method for analyzing images, an input image is provided to a computer and is processed therein with a first deep learning model so as to generate an output result for the input image; and applying a second deep learning model is applied to the input image to generate an output confidence score that is indicative of the reliability of any output result from the first deep learning model for the input image.

12 Claims, 5 Drawing Sheets

(56) References Cited

U.S. PATENT DOCUMENTS

| | | | |
|---|---|---|---|
| 2020/0027251 A1* | 1/2020 | Demesmaeker | G06T 11/006 |
| 2020/0074238 A1* | 3/2020 | Umeno | G06K 9/6215 |
| 2020/0074622 A1* | 3/2020 | Yang | G06N 3/08 |
| 2020/0104720 A1* | 4/2020 | Bao | G06K 9/6256 |
| 2020/0143240 A1* | 5/2020 | Baker | G06N 3/04 |
| 2020/0202507 A1* | 6/2020 | Ceccaldi | G06N 3/0454 |
| 2020/0250812 A1* | 8/2020 | Ceccaldi | G16H 50/70 |
| 2020/0356808 A1* | 11/2020 | Kim | G06N 3/088 |

* cited by examiner

METHOD AND SYSTEM FOR GENERATING A CONFIDENCE SCORE USING DEEP LEARNING MODEL

BACKGROUND OF THE INVENTION

Field of the Invention

The present invention relates to a method and system for analyzing images, for example analyzing medical images.

Description of the Prior Art

Deep learning (DL) methods are machine learning based approaches used to solve a wide variety of problems. As examples, DL methods may be used in medical imaging for specific tasks such as anomaly detection, tissue segmentation or image registration. In such DL methods, there are DL models which are typically trained on wide datasets of images. Nevertheless, the DL models may still not be effective in 100% of real situations, for example when they follow a specific training with limited datasets. This is a key concern when using the DL models in a clinical environment.

Therefore, there is a desire to provide an improved method and system for analyzing images using DL models.

SUMMARY OF THE INVENTION

To address these problems, the present invention provides a method for processing an image, the method comprising: receiving an input image which is to be processed by a first deep learning model to generate an output result for the input image; and applying a second deep learning model to an input image to generate an output confidence score which is indicative of the reliability of any output result from the first deep learning model for the input image.

Each deep learning model may be a machine learning model comprising a network capable of learning from data. The learning may be supervised, semi-supervised or unsupervised and the data may be unstructured or unlabeled.

The first deep learning model may be termed the main task model because it is the task which is performed on the input image, e.g. anomaly detection, scan de-noising, image reconstruction and image to image generation. A problem with such models is that they may predict incorrect results without being aware of the failure. Accordingly, usage of deep learning models in certain fields, e.g. medical fields, where reliability is key, is often very limited due to the lack of a confidence score. This often leads to a user manually checking the predictions from the first deep learning model.

The second deep learning model may be termed a usability check model because it generates an output confidence score which is a check for the first deep learning model. Using a second, independent deep learning model to check the first deep learning model may be more reliable than using the first deep learning model itself to produce its own confidence score. As explained in more detail below, the second deep learning model may provide a confidence score linked to the training data or a confidence score linked more directly to the first deep learning model. Both types of confidence scores may also be used. Such confidence scores may perform better and be more stable than other standard metrics such as prediction metrics which are generated for deep learning models.

Furthermore, the generation (i.e. calculation) of such confidence scores means that the user can be more confident that the results from the first deep learning model can be trusted if the confidence score is high and within a predefined confidence interval. They are also made aware that they need to run additional analysis, e.g. a manual review, if the confidence score is outside the confidence interval. For example, the predefined confidence interval may be an absolute interval and may be based on a linear interpretation of the confidence score. The confidence interval, like the confidence score itself, may be considered indicative for a better user experience. A number of confidence intervals may be defined; wherein each confidence interval has a different range.

The first deep learning model and the second deep learning model may have been trained on the same training data. In this way, the second deep learning model generates an output confidence score which is related to the data. Applying the second deep learning model to generate an output confidence score may comprise generating a reconstructed image; and comparing the reconstructed image with the input image to generate the output confidence score. For example, the second deep learning model may be an auto-encoder which comprises an encoding module to generate an intermediate (encoded) result and a decoding module to generate a reconstructed image from the intermediate result. Generating the output confidence score may be done using any suitable metric, e.g. mean square error or structural similarity.

When the first and second deep learning models have been trained on the same data, the further an input image is outside the distribution of images within the training data, the more unlikely it is that the input image can be reconstructed and the lower the output confidence score. The output result for the first deep learning model is also more uncertain and this is captured in the lower output confidence score. Similarly, if the input image is within the distribution of images within the training data, the more likely it is that the input image can be reconstructed and the higher the output confidence score will be, to reflect that the output result for the first deep learning model is more certain. Thus, the output confidence score is indicative of the behavior of the first deep learning model on a particular input image.

The method may include determining whether the output confidence score is within a confidence interval. When it is determined that the output confidence score is outside a confidence interval, an alert, e.g. an audio/visual signal, may be output to the user. The level of the alert may be dependent on the range of the confidence interval. For example, a high alert (e.g. an urgent message) may be output when it is determined that the output confidence score is outside a relatively narrow confidence interval and a low-grade alert (e.g. a different message) when it is determined that the output confidence score is outside a relatively broad confidence interval. In response to determining that the output confidence score is within a confidence interval, the method may further comprise applying the first deep learning model to the input image to generate the output result. In other words, the first deep learning model may not be applied when it is determined that the model is going to produce uncertain results. Alternatively, the method may further comprise applying the first deep learning model to the input image regardless of the confidence score but the method may then comprise simultaneously outputting the output confidence score and the output result. In this way, a user is still able to determine whether or not the results are trustworthy.

As an alternative to generating a confidence score which is based on the data, a confidence score which relates to the first model may be generated. Applying the second deep learning model to generate an output confidence score may thus comprise generating a reconstructed image; applying the first deep learning model to the reconstructed image to generate an output result for the reconstructed image; calculating a first loss value based on the input image and the output result using the reconstructed image, and generating the output confidence score using the first loss value. In this scenario, the two models are effectively combined because the first model is applied to the outcome of the second model. This propagates any errors in the first model over the second model. The first loss value may be termed a main task loss. A second loss value may be calculated using the reconstructed image and the original input image. The second loss value may be termed a reconstruction loss because it is compared the reconstructed image generated by the second model to the original input image. The output confidence score may be generated using both the first loss value and the second loss value. The second deep learning model may be an autoencoder.

It will be appreciated that both types of confidence scores may be used together. The second deep learning model may thus generate an output confidence score based on the data as described above. A third deep learning model may be used to generate an output confidence score based on the first model as described above. The method may thus include applying a third deep learning model to generate a second output confidence score by generating a reconstructed image; applying the first deep learning model to the reconstructed image; calculating a first loss value based on the input image and the output result using the reconstructed image, and generating the second output confidence score using the first loss value. As above, the first loss value may be termed a main task loss. The third deep learning model may be an autoencoder. A second loss value may be calculated using the reconstructed image and the original image. The second loss value may be termed a reconstruction loss. The output confidence score may be generated using both the first loss value and the second loss value.

According to another aspect of the invention, there is provided a (non-transitory) computer readable medium carrying processor control code which when implemented in a system (e.g. an image processor) causes the system to carry out the method described above.

Another aspect of the present invention is an image processing system for processing an image. The system includes an image processor which is configured to carry out the method described above. The system may also include an image capture device configured to capture an image and this is the input image which may be received by the image processor. The system may also include a user interface configured to display at least one of the output confidence score and the output result which are generated by the image processor.

DESCRIPTION OF THE PREFERRED EMBODIMENTS

Figure 1:
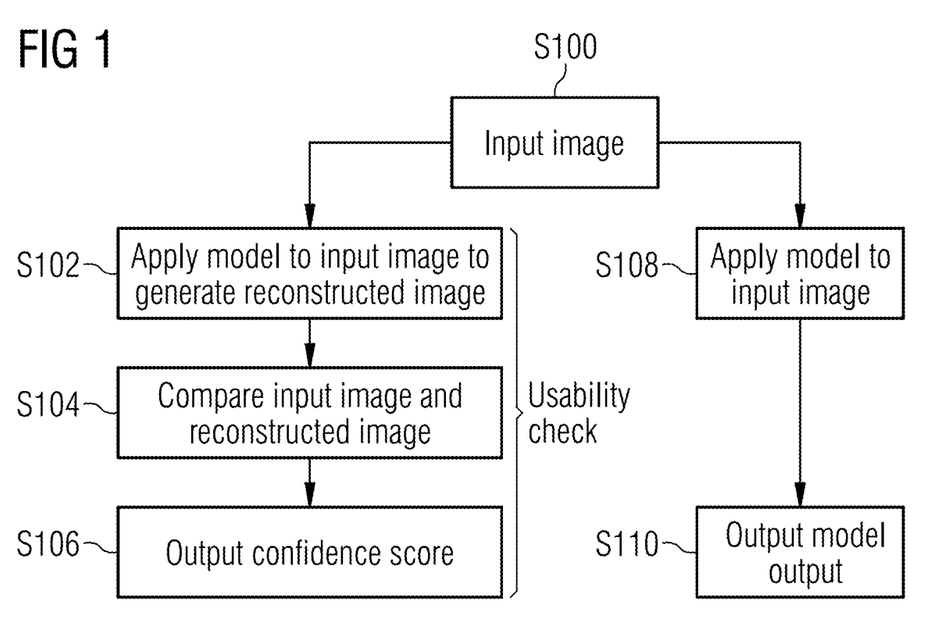
FIG. 1 is a flowchart of a method implementing according to one aspect of the invention.

FIG. 1 is a flowchart for analyzing an image, e.g. a medical image. In a first step, an image is entered into a computer or processor (S100). The input image is then processed by a first deep learning model which may be termed the main task model (S108) and which is being used to produce an output, e.g. by a radiologist to detect an anomaly from an image in the form of a scan. As shown the output from the main task model may be output to a user, e.g. to the clinician (S110). For example, the output may confirm that there is an anomaly in the scan which needs further investigation. However, the user needs to understand whether or not the DL model has produced a reliable output.

The method thus also comprises a sequence of steps which may be considered to be a "usability check". The same input image is processed by a second deep learning model which may be termed a usability check model (S102). The usability check model deconstructs the input image and then reconstructs the input image from the deconstructed result to form a reconstructed image. The next step is then to compare the reconstructed image to the input image (S104). Both the usability check model and the main task model have been trained using the same data. Accordingly, if the usability check model is unable to reconstruct the input image, i.e. the reconstructed image is too different from the input image, it is likely that the input image is too far from the distribution of training images and thus the output from the main task model is also likely to be unreliable and its output uncertain.

The comparison may include calculating a confidence score based on the differences between the reconstructed and input images. As explained above, such a confidence score is indicative of the likelihood that the main task model is reliable. The more different the reconstructed image is from the original input image, the lower the confidence score and hence there is less confidence in the main task model to produce good results and vice versa. Merely as examples, the confidence score may be calculated using mean square error (MSE) or structural similarity (SSIM) and suitable equations are set out below. However, it will be appreciated that any suitable method that provides a confidence score may be used.

$$MSE \text{ Mean(input}-\text{recon)}^2$$

$$SSIM \frac{(2\mu_i\mu_r + c1)(2\sigma_i\sigma_r + c2)(2cov_{ir} + c3)}{(u_i^2 + u_r^2 + c1)(\sigma_i^2 + \sigma_r^2 + c2)(\sigma_i\sigma_r + c3)}$$

where μ is the mean, σ is the variance and cn are constants.

The confidence score is then emitted as an output to the user (S106). As shown the usability check model can be applied simultaneously with the main task model and thus the confidence score can be output with the results from the main task model (S112). By emitting the confidence score with the results, the user is provided with an indication of the reliability of the results. Accordingly, if a high confidence score is predicted, the user can be confident that the results are reasonably accurate and does not need to perform an alternative confirmatory analysis of the image. Alternatively, the user may be alerted if the model is likely to predict erroneous or unreliable results and may thus analyze the image using a different technique (e.g. manual review).

As an alternative, the main task model may only be applied after the usability check model has been performed. For example, if the confidence score is outside a confidence interval, the method may comprise issuing an alert to the user that the main task model will not provide reliable results and a recommendation that an alternative method must be used to analyze the images. In either alternative, the application of the usability check model is totally detached from the application of the main task model.

Figure 2:
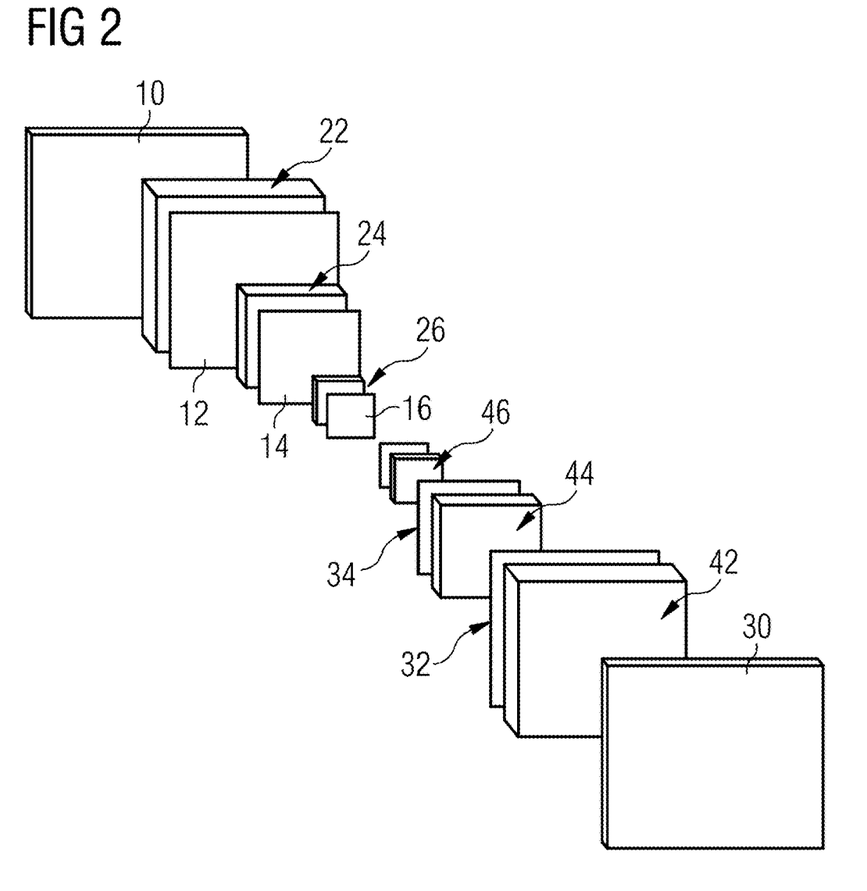
FIG. 2 is a schematic block diagram of part of the method of FIG. 1.

FIG. 2 is a schematic block diagram illustrating the second DL model which is applied to an input image 10 to generate a reconstructed image 30. As an example, the second DL model may be an autoencoder, i.e. a neural network comprising an encoder, a decoder and a loss function. Autoencoders may be considered to be generative models of data which are fit to large data-sets. A suitable example is a variational auto encoder (VAE). The autoencoder may be based on convolution layers and may thus comprise a number of convolution blocks 22, 24, 26, 42, 44, 46 and a number of pooling layers 12, 14, 16, 32, 34. As schematically illustrated, a first set of convolution blocks 22, 24, 26 successfully encode the image and as illustrated reduce the data in each subsequent pooling layer 12, 14, 16 with the final pooling layer 16 effectively being an intermediate (encoded) result. A second set of convolution blocks 46, 44, 42 are then applied sequentially to decode the final pooling layer 16 which is output from the encoder. Each convolution block in the decoder may be considered to increase the data in each subsequent pooling layer 34, 32 until the final layer is the reconstructed image 30. It will be appreciated that the number of convolution blocks and layers in the encoder and decoder is merely illustrative and any suitable number may be used.

Each convolution block may have one or more of a convolution layer, a normalization layer and a leaky rectified linear unit (ReLU) layer. The pooling layer may implement average pooling. Such an autoencoder may estimate the probability density function of the training data. As an example, the loss function used in the autoencoder may be based on the latent space Q and may be a sum of the losses produced by the latent space distribution parameters ($L_{ls}$) and the losses from the output reconstructed image ($L_{out}$). The loss $L_{ls}$ may be calculated from $$L_{ls}=E_z[\log P(\text{input}|z)]-KL[Q(z|\text{input})\|P(z)]$$

Where KL is the Kullback-Leibler divergence over the multivariate standard Gaussian z, Q is the latent space, Q(z|input) is the supervised distribution parameters, P is the Gaussian probability distribution and $E_z$ is the common operator—probabilistic expectation.

The output from the usability check model may be the reconstructed image and/or may be an output $L_{out}$ which allows supervision of the output with the input, e.g.

$$L_{out}=L_1(\text{input},\text{output})$$

Figure 3:
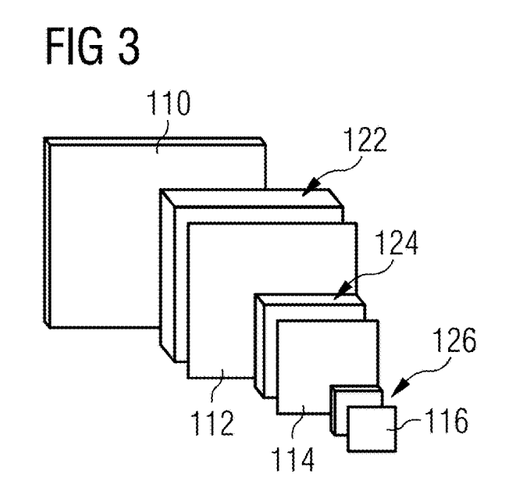
FIG. 3 is a schematic block diagram of another part of the method of FIG. 1.

FIG. 3 is a schematic block diagram illustrating the first DL model (main task model) which is applied to an input image 110 to generate a result, for example detection of an anomaly, de-noising a scan, reconstructing an image or image to image generation. As set out above, the two DL models may have been trained on the same data. They may also be of similar types. For example, as shown in FIG. 3, the usability check model may also be an autoencoder based on convolution layers and may thus comprise a number of convolution blocks 122, 124, 126 and a number of pooling layers 112, 114, 116. In this case, the output layer 116 has the results that are presented to a user. There is no need to reconstruct the original input image.

As explained above, the usability check model and the main task model may be applied separately but have been trained on the same data. In such a case, the usability check model provides a confidence score related to the training data which is also indicative of the likelihood of a successful result. As an alternative, or in addition, a usability check which checks the likelihood of a successful result relative to the main task model may also be used.

Figure 4:
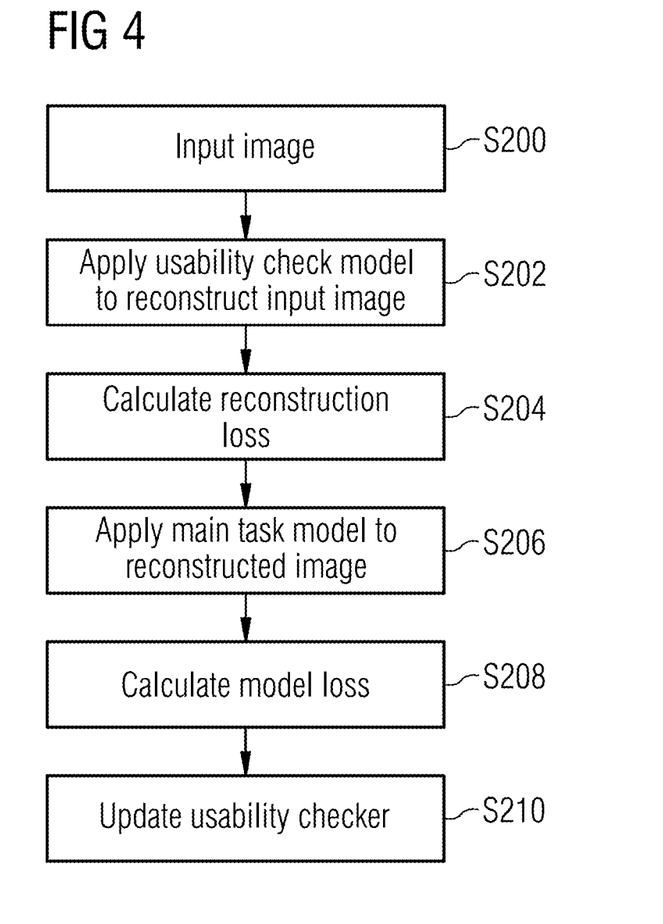
FIG. 4 is a flowchart of a complementary method to the method of FIG. 1

FIG. 4 is a flowchart illustrating the steps in implementing a usability check relative to the results of the main task model. In a first step, an image is input (S200). The usability check model described above is then applied to the image to generate a reconstructed image (S202). A reconstruction loss may also be calculated by comparing the reconstructed image from the usability check model with the original input image (S204). For example, the reconstruction loss may be calculated as the loss in the autoencoder (e.g. VAE) as described above using mean square error or structural similarity. The reconstruction loss may be calculated by determining the loss in the VAE combined with a Least Absolute Deviations (L1) loss. Any suitable loss functions may be used.

The reconstructed image is then provided as an input to the main task model (S206) so as to generate a result, i.e. a clinical diagnosis, based on the reconstructed image. A model loss (also termed a main task loss) is calculated (S208) by comparing the output from the main task model applied to the reconstructed image with the original input image. The calculation of the model loss will be dependent on the nature of the model and the problem it is solving. Any suitable loss function may be used.

Two different losses may thus be calculated. As shown in the Figure, they are calculated sequentially but it will be appreciated that they can be calculated simultaneously or in a different order.

The calculated losses may be combined to generate a second confidence score which is indicative of the likelihood that the main task model will generate correct results. This can then be used to update the usability checker (S210). DL models may use back propagation of their errors to update themselves. The calculation of the model losses as described above (in particular the main task loss), allows any errors in the main task model to be propagated further than its own input (i.e. the image which is provided as an input to the main task model) by propagating the error over the usability check model too. Thus, we may have a first confidence score generated as described in relation to FIG. 1 which is related to the data and a second confidence score as described in relation to FIG. 4 which is related to the main task model itself. Both could be used together but it is only necessary to have a single prediction from the usability checkers to provide the desired improvement. By combining the losses, the full system is likely to be more stable. Moreover, the combination means that the reconstruction model is better correlated with the main task model because it will also use its loss to be updated.

Figure 5:
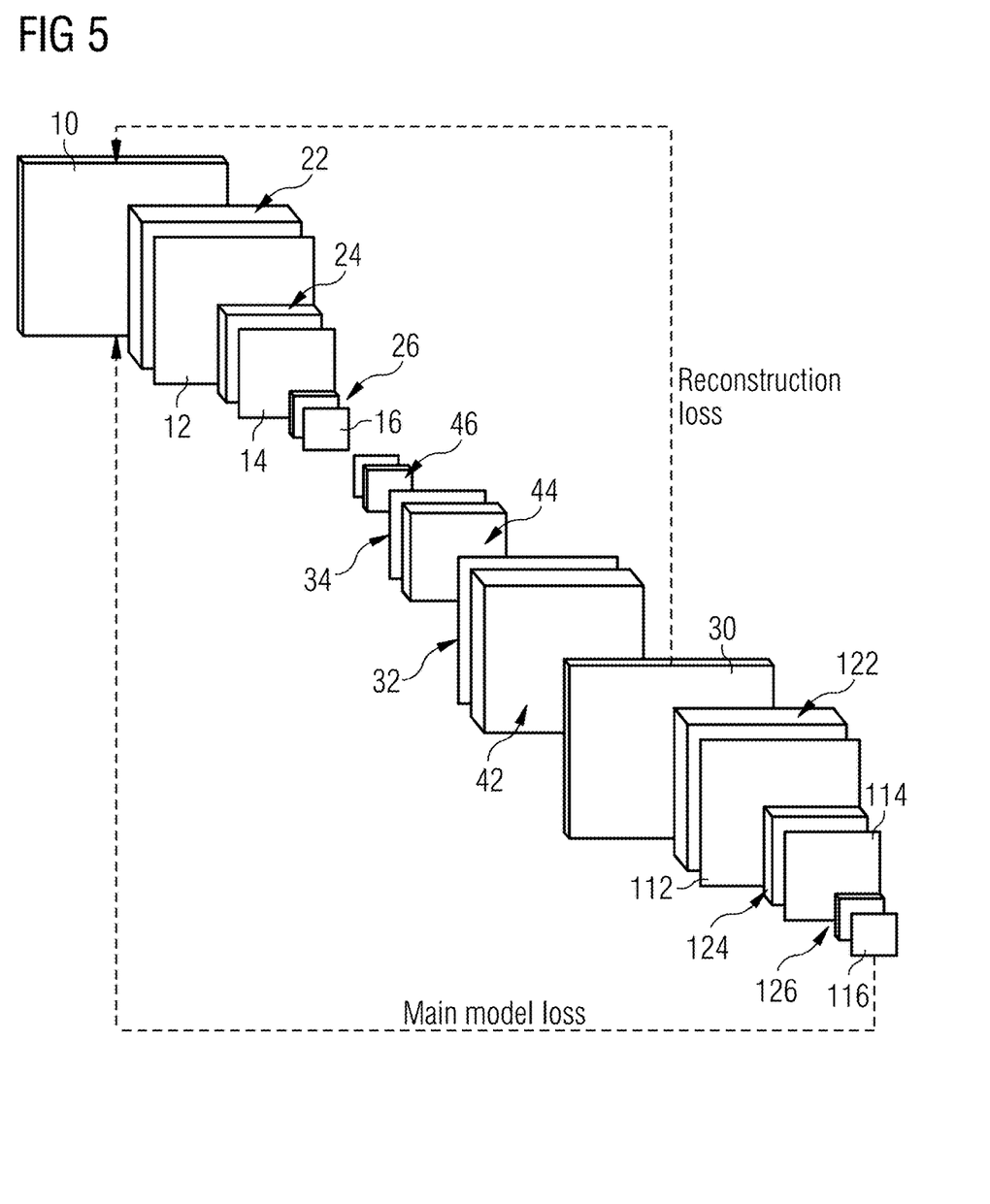
FIG. 5 shows a schematic block diagram of the method of FIG. 4.

FIG. 5 is a schematic illustration of the method of FIG. 4. In line with the arrangement illustrated in FIG. 2, the usability check model is illustrated as an autoencoder based on convolution layers and comprises a plurality of convolution blocks 22, 24, 26, 42, 44, 46 and a plurality of pooling layers 12, 14, 16, 32, 34. The usability check model is applied to an input image 10 to generate a reconstructed image 30. The main task model is then applied to the reconstructed image 30. As shown in FIG. 3, the main task model is also a DL model having a number of convolution blocks 122, 124, 126 and a plurality of pooling layers 112, 114, 116. In this case, the output layer 116 has the output results that are presented to a user and in this arrangement, they are based on the reconstructed image rather than an original input image.

Figure 6:
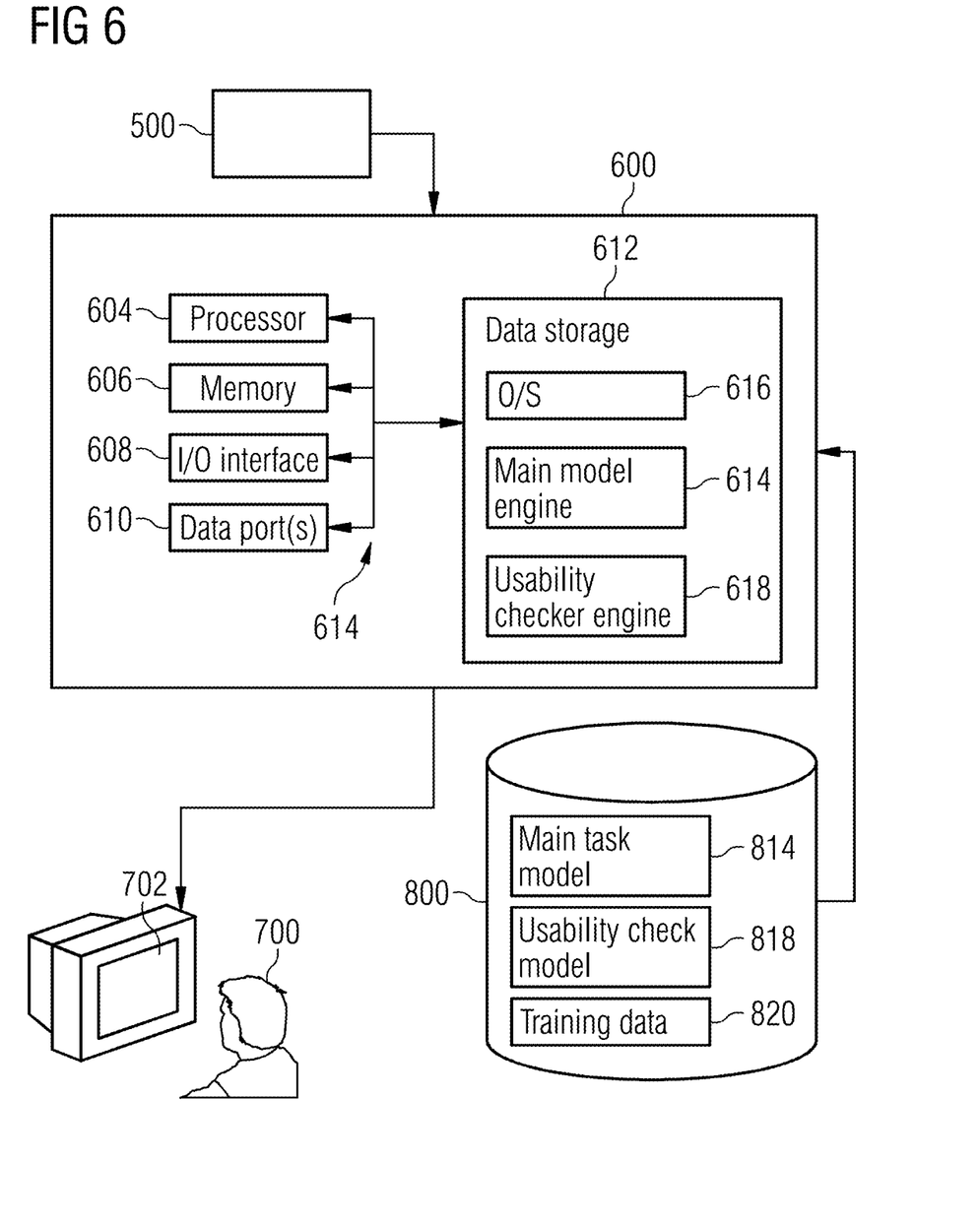
FIG. 6 is a block diagram of the internal components of a module which can be used to carry out the methods above.

FIG. 6 is a schematic block diagram illustrating the components of the image processing system. The system includes an image processor 600 that performs the methods of FIGS. 1 and 4. An imaging system 500, e.g. an X-ray machine, a scanner or the like, captures an image which is sent to the image processor 600. The outputs from the image processing, i.e. the confidence score(s) and the results of the main task model may be provided as an output to a user 700 via any suitable user interface 702, e.g. a screen on a computer or other electronic device. The image processor 600 may also be connected to a database 800, which stores for example the training data 820 which is used to train the models, the main task model 814 and the usability check model(s) 816.

The image processor 600 may be formed from one or more servers and the steps (or tasks) in FIGS. 1 and 4 may be split across the one or more servers or the cloud. The image processor 600 may include one or more processors 604, one or more memory devices 606 (generically referred to herein as memory 606), one or more input/output ("I/O") interface(s) 608, one or more data ports 610, and data storage 612. The image processor 600 may further include one or more buses 614 that functionally couple various components of the image processor 600.

The data storage 612 may store one or more operating systems (O/S) 616; and one or more program modules, applications, engines, computer-executable code, scripts, or the like such as, for example, a main model engine 616 and a usability checker model engine 618. The main model engine 616 may apply the model as illustrated in FIG. 3 and the usability checker model 618 may apply one or more of the models illustrated in FIGS. 2 and 5. Any of the components depicted as being stored in data storage 612 may include any combination of software, firmware, and/or hardware. The software and/or firmware may include computer-executable code, instructions, or the like that may be loaded into the memory 606 for execution by one or more of the processor(s) 604 to perform any of the operations described earlier in connection with correspondingly named engines.

The bus(es) 614 may include at least one of a system bus, a memory bus, an address bus, or a message bus, and may permit exchange of information (e.g., data (including computer-executable code), signaling, etc.) between various components of the image processor 600. The bus(es) 614 may include, without limitation, a memory bus or a memory controller, a peripheral bus, an accelerated graphics port, and so forth. The bus(es) 614 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 606 of the image processor 600 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 606 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 606 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 612 and/or the database 800 may include removable storage and/or non-removable storage including, but not limited to, magnetic storage, optical disk storage, and/or tape storage. The data storage 612 and/or the database 800 may provide non-volatile storage of computer-executable instructions and other data. The memory 606, the database 800 and the data storage 612, removable and/or non-removable, are examples of computer-readable storage media (CRSM).

The data storage 612 may store computer-executable code, instructions, or the like that may be loadable into the memory 606 and executable by the processor(s) 604 to cause the processor(s) 604 to perform or initiate various operations. The data storage 612 may additionally store data that may be copied to memory 606 for use by the processor(s) 604 during the execution of the computer-executable instructions. Moreover, output data generated as a result of execution of the computer-executable instructions by the processor(s) 604 may be stored initially in memory 606, and may ultimately be copied to data storage 612 for non-volatile storage.

The data storage 612 may further store various types of data utilized by components of the image processor 600. Any data stored in the data storage 612 may be loaded into the memory 606 for use by the processor(s) 604 in executing computer-executable code. In addition, any data depicted as being stored in the data storage 612 may potentially be stored in one or more of the datastores and may be accessed and loaded in the memory 606 for use by the processor(s) 604 in executing computer-executable code.

The processor(s) 604 may be configured to access the memory 606 and execute computer-executable instructions loaded therein. For example, the processor(s) 604 may be configured to execute computer-executable instructions of the various program modules, applications, engines, or the like of the system to cause or facilitate various operations to be performed in accordance with one or more embodiments of the disclosure. The processor(s) 604 may include any suitable processing unit capable of accepting data as input, processing the input data in accordance with stored computer-executable instructions, and generating output data. The processor(s) 604 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 604 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 604 may be capable of supporting any of a variety of instruction sets.

Referring now to other illustrative components depicted as being stored in the data storage 612, the O/S 616 may be loaded from the data storage 612 into the memory 606 and may provide an interface between other application software executing on the image processor 600 and hardware resources of the image processor 600. More specifically, the O/S 616 may include a set of computer-executable instructions for managing hardware resources of the system and for providing common services to other application programs (e.g., managing memory allocation among various application programs). In certain example embodiments, the O/S 616 may control execution of one or more of the program modules depicted as being stored in the data storage 612. The O/S 616 may include any operating system now known or which may be developed in the future including, but not limited to, any server operating system, any mainframe operating system, or any other proprietary or non-proprietary operating system.

Referring now to other illustrative components of the image processor 600, the input/output (I/O) interface(s) 608 may facilitate the receipt of input information by the image processor 600 from one or more I/O devices as well as the output of information from the image processor 600 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the image processor 600 or may be separate. The I/O devices may further include, for example, any number of peripheral devices such as data storage devices, printing devices, and so forth.

The I/O interface(s) 608 may also include an interface for an external peripheral device connection such as universal serial bus (USB), FireWire, Thunderbolt, Ethernet port or other connection protocol that may connect to one or more networks. The I/O interface(s) 608 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The image processor 600 may further include one or more data ports 610 via which the image processor 600 may communicate with any of the processing modules. The data ports(s) 610 may enable communication with the image capture device 500 and the database 800.

It should be appreciated that the engines and the program modules depicted in the Figures are merely illustrative and not exhaustive and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the system and/or hosted on other computing device(s) accessible via one or more of the network(s), may be provided to support the provided functionality, and/or additional or alternate functionality. Further, functionality may be modularized differently such that processing described as being supported collectively by the collection of engines or the collection of program modules may be performed by a fewer or greater number of engines or program modules, or functionality described as being supported by any particular engine or module may be supported, at least in part, by another engine or program module. In addition, engines or program modules that support the functionality described herein may form part of one or more applications executable across any number of devices of the system in accordance with any suitable computing model such as, for example, a client-server model, a peer-to-peer model, and so forth. In addition, any of the functionality described as being supported by any of the engines or program modules may be implemented, at least partially, in hardware and/or firmware across any number of devices.

It should further be appreciated that the system may include alternate and/or additional hardware, software, or firmware components beyond those described or depicted without departing from the scope of the disclosure. More particularly, it should be appreciated that software, firmware, or hardware components depicted as forming part of the system are merely illustrative and that some components may not be present or additional components may be provided in various embodiments. While various illustrative engines have been depicted and described as software engines or program modules, it should be appreciated that functionality described as being supported by the engines or modules may be enabled by any combination of hardware, software, and/or firmware. It should further be appreciated that each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain engines modules may be depicted or described as sub-engines or sub-modules of another engine or module, in certain embodiments, such engines or modules may be provided as independent engines or modules or as sub-engines or sub-modules of other engines or modules.

The operations described and depicted in the illustrative methods of FIGS. 1 and 4 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 1 and 4 may be performed.

Although specific embodiments of the disclosure have been described, those of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, those of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Program modules, applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The invention claimed is:

1. A method for processing an image, the method comprising:
receiving an input image and process the input image with a first deep learning model to generate an output result for the input image; and
applying a second deep learning model to the input image to generate an output confidence score which is indicative of the reliability of the output result from the first deep learning model for the input image, wherein applying the second deep learning model to generate an output confidence score comprises:
generating a reconstructed image; and
comparing the reconstructed image with the input image to generate the output confidence score.

2. The method of claim 1, wherein the first deep learning model and the second deep learning model have been trained on the same training data.

3. The method of claim 1, comprising generating the output confidence score using mean square error or structural similarity.

4. The method of claim 1 further comprising determining whether the output confidence score is within a confidence interval.

5. The method of claim 4, further comprising outputting an alert when it is determined that the output confidence score is outside a confidence interval.

6. The method of claim 5, further comprising outputting a high alert when it is determined that the output confidence score is outside a first confidence interval and outputting a low alert when it is determined that the output confidence score is outside a second confidence interval that is broader than the first confidence interval.

7. The method of claim 1, further comprising applying the first deep learning model to the input image and simultaneously outputting the output confidence score and the output result.

8. The method of claim 1, wherein the second deep learning model is an autoencoder.

9. A non-transitory, computer-readable data storage medium encoded with programming instructions that, when the storage medium is loaded into a computer, cause the computer to:
receive an input image and process the input image with a first deep learning model to generate an output result for the input image; and
apply a second deep learning model to the input image to generate an output confidence score which is indicative of the reliability of the output result from the first deep learning model for the input image
apply a third deep learning model to generate a second output confidence score by generating a reconstructed image, applying the first deep learning model to the reconstructed image, calculating a first loss value based on the input image and the output result using the reconstructed image, and generating the second output confidence score using the first loss value.

10. The non-transitory, computer-readable data storage medium of claim 9, wherein the programming instructions, when the storage medium is loaded into the computer, cause the computer to calculate a second loss value using the reconstructed image and the input image and generate the output confidence score using both the first loss value and the second loss value.

11. An image processing system comprising
an image capture device configured to capture an image;
an image processor configured to:
receive said image from the image capture device as an input image,
process said input image with a first deep learning model to generate an output result for the input image, and
apply a second deep learning model to the input image to generate an output confidence score that is indicative of the reliability of the output result from the first deep learning model for the input image by generating a reconstructed image, applying the first deep learning model to the reconstructed image, calculating a first loss value based on the input image and the output result using the reconstructed image, and generating the output confidence score using the first loss value; and
a user interface configured to display at least one of the output confidence score and the output result that are generated by the image processor.

12. The image processing system of claim 11, wherein the applying the second deep learning model to generate an output confidence score further comprises calculating a second loss value using the reconstructed image and the input image and generating the output confidence score using both the first loss value and the second loss value.

* * * * *